(12) United States Patent
Strasly et al.

(10) Patent No.: US 8,753,393 B2
(45) Date of Patent: Jun. 17, 2014

(54) METHOD FOR DETOXIFYING A BIOLOGICAL TISSUE

(75) Inventors: Marina Strasly, Baldissero Torinese (IT); Vincenzo Cassolaro, Saluggia (IT)

(73) Assignee: Sorin Group Italia S.r.l., Milan (IT)

( * ) Notice: Subject to any disclaimer, the term of this patent is extended or adjusted under 35 U.S.C. 154(b) by 164 days.

(21) Appl. No.: 13/154,856

(22) Filed: Jun. 7, 2011

(65) Prior Publication Data

US 2011/0306124 A1 Dec. 15, 2011

(30) Foreign Application Priority Data

Jun. 9, 2010 (IT) ............................... TO2010A0486
May 26, 2011 (EP) ..................................... 11167681

(51) Int. Cl.
- *A61F 2/08* (2006.01)
- *A01N 1/00* (2006.01)
- *A01N 1/02* (2006.01)

(52) U.S. Cl.
USPC ........................................ 623/13.17; 435/1.1

(58) Field of Classification Search
USPC ....................................................... 623/13.17
See application file for complete search history.

(56) References Cited

U.S. PATENT DOCUMENTS

| | | | | |
|---|---|---|---|---|
| 4,755,593 | A * | 7/1988 | Lauren | 530/356 |
| 5,873,812 | A | 2/1999 | Ciana et al. | |
| 6,479,079 | B1 | 11/2002 | Pathak et al. | |
| 2006/0110370 | A1 | 5/2006 | Pathak et al. | |
| 2006/0193885 | A1 | 8/2006 | Neethling et al. | |
| 2007/0269478 | A1 | 11/2007 | Piconi et al. | |
| 2008/0302372 | A1 * | 12/2008 | Davidson et al. | 128/898 |
| 2009/0164005 | A1 * | 6/2009 | Dove et al. | 623/2.13 |
| 2011/0306123 | A1 | 12/2011 | Strasly et al. | |
| 2011/0306124 | A1 | 12/2011 | Strasly et al. | |

FOREIGN PATENT DOCUMENTS

EP 0795337 A2 9/1997

OTHER PUBLICATIONS

"Biological Buffers" from AppliChem, pp. 1-20, 2008.*
European Search Report and Opinion issued in EP Application No. 11167681, dated Oct. 28, 2011, 5 pages.
European Search Report and Opinion issued in EP Application No. 11167695, dated Nov. 7, 2011, 6 pages.
Italian Search Report and Written Opinion issued in IT Application No. TO2010A000486, completed Jan. 17, 2011, 7 pages.
Italian Search Report and Written Opinion issued in IT Application No. TO2010A000487, Jan. 21, 2011, 9 pages.
Pathak, Chandrashekar P. et al., "Treatment of bioprosthetic heart valve tissue with logn chain alcohol solution to lower calcification potential", J. Biomed. Mater. Res., 69A; 140-144, 2004.
Pettenazzo, Elena et al., "Octanediol treatement of glutaraldehyde fixed bovine pericardium: evidence of anticalcification efficacy in the subcutaneous rat model", European Jouran of Cardio-thoracic Surgery 34 (2008) 418-422.
Stacchino, Carla et al., "Detoxification Process for Glutaraldehyde-treated Bovine pericardium: Biological, Chemical and Mechanical Characterization", Journal of Heart Valve Disease, vol. 7, No. 2, Mar. 1998, pp. 190-194.

* cited by examiner

*Primary Examiner* — Thaian N Ton
(74) *Attorney, Agent, or Firm* — Faegre Baker Daniels LLP

(57) ABSTRACT

Biological tissues may be prepared for use in biological prostheses. The biological tissue may be fixated with glutaraldehyde and may be subjected to successive treatment of the tissue with a solution containing taurine to neutralize excess aldehyde groups that remain free after fixation.

14 Claims, 2 Drawing Sheets

METHOD FOR DETOXIFYING A BIOLOGICAL TISSUE

RELATED APPLICATION

This application claims priority to Italian Patent Application No. IT TO2010A000486 filed Jun. 9, 2010, and claims priority to European Application No. 11167681, filed May 26, 2011, both applications are incorporated by reference herein in their entirety.

TECHNICAL FIELD

The present invention is generally directed to a method for detoxifying biological tissue for use in biological prostheses such as prosthetic valves and more particularly to a method for detoxifying biological tissue for use in prosthetic cardiac valves.

BACKGROUND

Biological prostheses are medical devices that utilize animal tissues. Examples of suitable animal tissues include bovine, porcine, ovine and equine. Depending on the various medical uses, the biological tissue include cardiac valves, pericardium, tendons, ligaments, dura mater, skin, veins, etc.

The animal tissues used in biological prostheses are formed primarily of collagen, a protein with a structural unit represented by three polypeptide chains that associate to form a triple helix. Collagen molecules assemble to form microfibrils that in turn assemble to form fibrils that, arranged in corrugated or parallel bundles, give rise to true collagen fibers. Such tissues have good resistance to traction and are flexible but substantially inextensible.

Animal tissues used in biological prostheses are first subjected to numerous washings to eliminate traces of blood and a careful removal of adipose and ligamentous parts. However, cells or cellular residues from the animal donor can remain trapped in the structure of the tissue itself. As a result it is possible that the immune system of the host gives rise to a rejection phenomenon that can lead to the destruction of the tissue constituting the biological prosthesis.

An additional problem is degradation of the collagenous biological tissue once implanted in the host organism. For this reason, the biological tissues are subjected to a fixation treatment with the aim of protecting the tissue from such degradation phenomena and contributing to preventing the above-mentioned rejection phenomenon.

Among the substances used for the fixation of biological tissues, the most common is glutaraldehyde. This bifunctional molecule, carrying two aldehyde groups, is capable of stably binding together free amino groups of the amino acids that constitute the polypeptide chains both within one collagen molecule and between adjacent collagen molecules. In this way glutaraldehyde forms intra-chain and inter-chain bridge structures, causing the cross linking of biological tissue. Such cross linking protects the tissue from degradation by the host and confers favorable mechanical properties such as for example a better resistance to traction with respect to untreated tissue.

Glutaraldehyde is a highly bactericidal and virucidal substance; therefore, in addition to cross linking the tissue, the fixation step also provides at least a partial sterilization.

In addition, glutaraldehyde is capable of binding to the free amino residues of the membrane proteins of the cellular components still present, masking their antigenic potential and impeding immune activation phenomena and rejection by the host.

In spite of widespread use, glutaraldehyde has a disadvantage of being one of the factors that favors pathological calcification of implanted tissues. The calcium, present in the bodily fluids of the host organism, accumulates in proteinaceous tissue giving rise, for example in the case of biological cardiac valves, to a process that may represent one of the principle causes of valve failure. The calcium deposits can reduce the flexibility of the portion of biological tissue constituting the valve (or the so-called valve leaflets or cusps) and lead to laceration of the tissue itself, causing a partial or total loss of valve function.

The mechanism responsible for calcification is not yet completely known and is attributed to numerous factors; however, it is known that after glutaraldehyde fixation, aldehyde groups remaining free on the tissue can create binding sites for calcium.

In addition, the toxicity of such aldehyde residues can cause local inflammatory phenomena that lead to the necrosis of host cells. Destruction of the dead cells gives rise to cellular debris that, in turn, can constitute binding cites for calcium. Several types of molecules capable of neutralizing the aldehyde residues remaining free after the fixation process have been used to limit the process of tissue calcification. For example, the use of amino acids has been shown to have an anti calcification effect; in particular, U.S. Pat. No. 5,873,812 describes the use of amino carboxylic acids, such as for example homocysteic acid, in the preparation of aldehyde-fixed biological tissues. However, this method only partially neutralizes free aldehyde groups and thus does not resolve the problem.

SUMMARY

The present invention is directed to improved, more efficacious solutions that limit the calcification of biological tissues after implantation in the host.

In some embodiments, the present invention is directed to a method for treating a biological tissue for biological prostheses. The method includes a tissue fixation step and a detoxification step.

In some embodiments, the method for treating a biological tissue includes fixation of the biological tissue via a treatment with a glutaraldehyde solution and detoxifying the fixed biological tissues via a treatment with a taurine solution at a temperature that is in the range of about 30 to about 45 degrees Celsius.

In some embodiments, the results presented below show that the method described herein strongly reduces the number of free aldehyde groups present on fixed tissue, presenting an clear advantage with respect to methods that envision the detoxification of tissue by means of immersion in a solution containing homocysteic acid.

BRIEF DESCRIPTION OF THE FIGURES

The invention will now be described in detail, by way of non-limiting example only, with reference to the attached figures, in which.

DETAILED DESCRIPTION

Figure 1A:
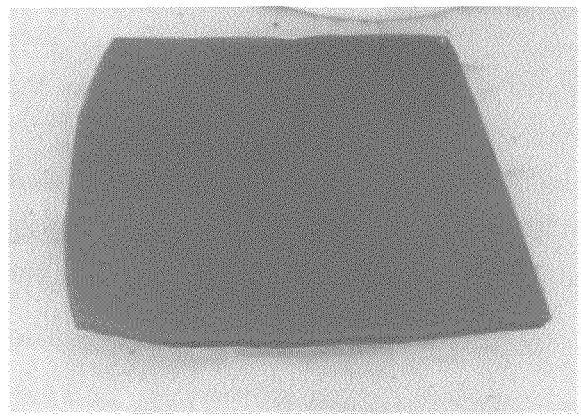
FIG. 1A shows fuchsine staining of a control sample fixed but not detoxified.

The invention will now be described in detail, by way of non-limiting example only, with reference to forming biological prosthetic cardiac valves. It is clear that the procedure described herein can be used for the detoxification of any other biological tissue destined for forming other biological prostheses that use, for example tendons, ligaments, dura mater, skin, veins, etc.

In the following description, numerous specific details are given to provide a thorough understanding of the embodiments. The embodiments can be practiced without one or more of the specific details, or with other methods, components, materials, etc. In other instances, well-known structures, materials or operations are not shown or described in detail to avoid obscuring certain aspects of the embodiments.

Reference throughout the present specification to "one embodiment" or "an embodiment" means that a particular feature, structure or characteristic described in connection with the embodiment is included in at least one embodiment. Thus, the phrase "in one embodiment" or "in an embodiment" in various places throughout the present specification are not necessarily all referring to the same embodiment. Furthermore, the details of features, structures, or characteristics may be combined in any suitable manner in one or more embodiments.

The headings provided herein are for convenience only and do not interpret the scope or meaning of the embodiments.

The present invention concerns a method for treating a biological tissue that includes two steps:
  i) Fixation of the biological tissue via treatment with a solution containing glutaraldehyde, and
  ii) Detoxification of the previously fixed biological tissue via treatment with a solution containing taurine.

In some embodiments, the fixation step includes immersion of the tissue in a solution containing glutaraldehyde for a period that varies between one minute and 3 days and a maximum of 13 days. Fixation cross links the tissue, which confers it with resistance to degradation and favorable mechanical properties.

In some embodiments, the detoxification step includes immersion of the previously fixed tissue in a solution containing taurine for a period that varies in a range from one minute to a few hours and a maximum of several days.

Taurine (also known as aminoethanesulfonic acid) has an amine group ($NH_2$) available to bond with the aldehyde groups of glutaraldehyde that remain free after the tissue fixation step. In particular, the present inventors discovered that the use of taurine in the detoxification step in place of homocysteic acid provides greater efficacy for neutralizing the aldehyde groups that remain free after glutaraldehyde fixation, therefore reducing in a highly efficacious way the number of sites of binding and accumulation of calcium on the biological tissue.

Biological tissues to be used for biological prosthetic cardiac valves, or bovine pericardium, equine or possibly pericardium of other animal species or porcine valves are harvested from authorized abattoirs and—transported to the laboratory—immersed in saline solution maintained on ice to avoid damage to the tissue before use.

The tissues are washed with saline solution to eliminate possible traces of blood, separated from possible adherent ligamentous and adipose parts, and then carefully selected on the basis of thickness and on the basis of the absence of evident defects such as dishomogeneity of thickness, presence of cuts, abrasions, etc.

The tissues are initially prefixed in a glutaraldehyde solution at room temperature in a volume/volume concentration that is in the range of 0.05% to 0.30% glutaraldehyde in phosphate buffer at a pH of 7.4 for a period of time that ranges from 3 to 13 hours. In some embodiments, the glutaraldehyde solution includes 0.20% glutaraldehyde After the prefixation step, in some embodiments, comes a step of cutting and shaping the tissue—according to known art techniques—to form, for example, cardiac valves. This step of shaping the tissue is irrelevant to the aims of the method object of the present description.

The method of fixation follows and is carried out by immersing the tissue in a solution containing glutaraldehyde at a concentration in the range 0.30% to 1.00%. In some embodiments, the solution contains glutaraldehyde at a concentration of 0.5%.

In some embodiments, the solution containing glutaraldehyde is an aqueous solution including a buffer selected from phosphate, citrate, acetate, HEPES, and borate. In some embodiments, the buffer is phosphate.

The pH of the glutaraldehyde-based solution is in the range of 5 to 8. In some embodiments, the pH of the glutaraldehyde-based solution is 7.4.

The fixing method is conducted at a temperature in the range 4° C. to 30° C. In some embodiments, the fixing method is conducted at room temperature (20° C.). The period of exposure of the tissue to the solution containing glutaraldehyde can vary in the range 1 to 20 days. In some embodiments, the exposure time is in the range of 3 to 13 days.

After the fixation step, the tissue is washed to remove residual glutaraldehyde that is not conjugated to the tissue. In some embodiments, the wash solution is a saline solution or a phosphate buffer pH 7-7.4 and is changed three times. Washing is performed for a period comprised in the range 30 minutes to 6 hours, with gentle agitation, at room temperature.

The fixed tissue is then detoxified using an aqueous solution containing taurine at a concentration w/v comprised in the range of 0.10% up to saturation of the solution. In some embodiments, the aqueous solution includes taurine at a w/v concentration of 0.20% to 1.00%. In some embodiments, the aqueous solution includes taurine at a concentration of 0.70% w/v.

In some embodiments, the aqueous taurine solution contains a buffer selected from phosphate, citrate, acetate, HEPES (4-(2-hydroxyethyl)-1-piperazine ethane sulfonic acid), and borate. In some embodiments, the buffer is phosphate. In some embodiments, the pH of the solution is in the range of 4 to 9. In some embodiments, the pH of the solution is 5 to 8. In some embodiments, the pH of the solution is 7.

In some embodiments, the detoxification step is conducted at a temperature in the range from room temperature (20° C.) to 50° C. In some embodiments, the detoxification step is conducted at a temperature that is in the range of 30° C. to 45° C. In some embodiments, the detoxification step takes place at a temperature of 40° C. In some embodiments, the period of immersion of the tissue in the taurine-containing solution may vary in the range from 2 to 96 hours. In some embodiments, the immersion period may be in the range of 12 to 48 hours. In some embodiments, the immersion period is 24 hours.

At the end of the detoxification step, the detoxified tissue is subjected to washing at room temperature, in phosphate buffer at pH 7, for about three hours, changing the wash solution three times.

The detoxified tissue is finally transferred to a conservation solution without aldehydes in phosphate buffer pH 7 containing preservatives such as parabens.

The efficacy of the method described herein, and therefore the occurrence of the reaction between the amino groups of the detoxifying molecule and the aldehyde groups present on the fixed tissue, is evaluated by staining of the aldehyde groups remaining free. The greater the staining intensity, the more numerous are the free aldehyde groups and, on the contrary, the weaker (or absent) the staining, the less numerous (or absent) are the free aldehyde groups present on the detoxified tissue. An example of a stain advantageously useful for such determination is fuchsine.

The results presented below demonstrate that taurine binds the free aldehyde groups present on fixed tissue more efficaciously than homocysteic acid. In addition, the present inventors have observed that better results are obtained by performing the detoxification step at a temperature above room temperature, that is, the number of free aldehyde groups present on the fixed tissue are greatly reduced.

The various preferred embodiments of the present invention will be described in detail below.

Materials and Methods

Harvesting and Fixation of Biological Tissue

The biological tissue, which were pieces of bovine pericardium harvested from authorized abattoirs, was placed in a saline solution maintained on ice and transported to the laboratory.

The tissues were washed with saline solution to eliminate possible traces of blood, separated from the any adherent ligamentous and adipose parts and were selected on the basis of the correct thickness and the absence of defects, such as dishomogeneity in thickness, presence of vascularizations, cuts, abrasions, etc.

The tissues were prefixed in a glutaraldehyde solution at 0.20% v/v in phosphate buffer pH 7.4, for a time variable in the range of 3 to 13 hours at room temperature.

After the prefixation step, the tissues were cut and shaped according to known art techniques—for making, for example, cardiac valves. Next the tissues were fixed for a period of time in the range 3 to 13 days at room temperature, in an aqueous solution of 0.50% v/v glutaraldehyde in phosphate buffer pH 7.4.

Detoxification of Tissue

The tissue to be detoxified was washed, to remove residual glutaraldehyde solution, in saline solution or in phosphate buffer pH 7.4 or pH 7, for about three hours, with gentle agitation, at room temperature. The wash solution was changed three times, using about 300 ml of solution each time for each piece of tissue with dimensions of about 10×5 cm.

The fixed solution was then detoxified using an aqueous solution containing taurine at a concentration (w/v) of about 0.70% in phosphate buffer pH 7. The detoxification step was conducted at room temperature (20° C.), 40° C. and 50° C., for a period of time of 24 hours, using about 200 ml of solution for each tissue.

At the end of the detoxification step, the detoxified tissue was washed at room temperature, in phosphate buffer at pH 7, for about three hours, changing the wash solution three times.

Finally, the detoxified tissue was transferred to a conservation solution without aldehydes containing preservatives, preferably parabens, in phosphate buffer pH 7.

With the aim of demonstrating the better efficacy of the detoxifying treatment with taurine compared to the known art, the present inventors have semi-quantitatively determined the number of free aldehyde groups in three samples of biological tissue treated as follows:

a first control sample (FIG. 1A) including biological tissue fixed with glutaraldehyde but not detoxified;

a second control sample (FIG. 1B) fixed with glutaraldehyde and detoxified with a solution containing homocysteic acid at a concentration (w/v) of 1.00% in phosphate buffer pH 7;

a third sample (FIG. 1C) fixed with glutaraldehyde and detoxified with a solution containing taurine at a concentration (w/v) equal to 0.70% in phosphate buffer pH 7.

The tissue samples were immersed in the detoxifying solutions for about 24 hours at room temperature with gentle agitation.

Figure 2A:
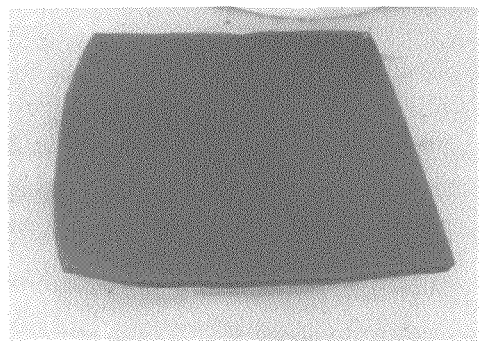
FIG. 2A fuchsine staining of a control sample fixed but not detoxified.
Figure 2B:
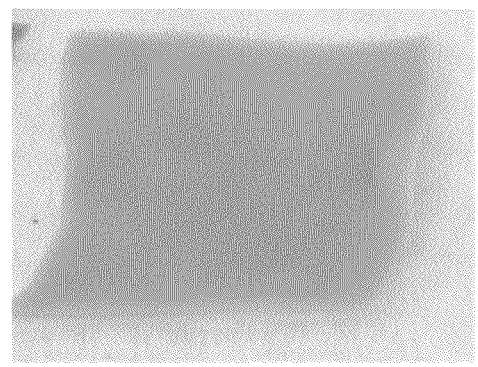
FIG. 2B shows fuchsine staining of a sample that was fixed and detoxified with a taurine solution at room temperature.
Figure 2C:
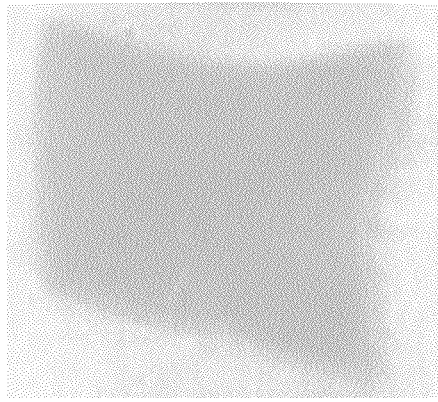
FIG. 2C shows fuchsine staining of a sample that was fixed and detoxified with a taurine solution at 40 degrees Celsius.
Figure 2D:
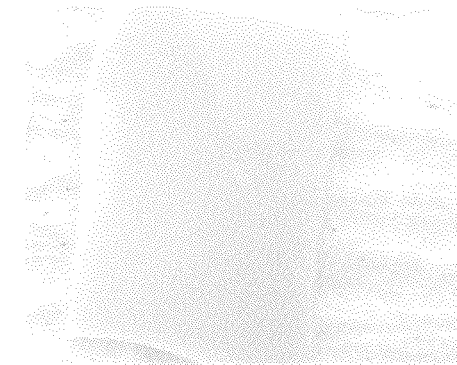
FIG. 2D shows fuchsine staining of a sample that was fixed and detoxified with a taurine solution at 50 degrees Celsius.

To verify the efficacy of the taurine detoxifying treatment with variation of the detoxifying solution temperature, the present inventors semi-quantitatively determined the number of free aldehyde groups in biological tissues treated as follows:

a first control sample (FIG. 2A) including biological tissue fixed with glutaraldehyde but not detoxified;

a second sample (FIG. 2B) fixed with glutaraldehyde and detoxified with a solution containing taurine at a temperature of 20° C.;

a third sample (FIG. 2C) fixed with glutaraldehyde and detoxified with a solution containing taurine at a temperature of 40° C.; and a fourth sample (FIG. 2D) fixed with glutaraldehyde and detoxified with a solution containing taurine at a temperature of 50° C.

The samples were immersed in the detoxifying solution for about 24 hours with gentle agitation both at room temperature and at 40° C.; the fourth sample detoxified at 50° C. was maintained immersed for 7-8 hours with gentle agitation.

About 200 ml of detoxifying solution were used for each sample.

At the end of the treatment all samples were washed at room temperature in phosphate buffer at pH 7, for about three hours, changing the wash solution three times and using about 300 ml of solution for each sample at each change.

All samples were then transferred to a phosphate buffer solution pH 7 containing preservatives such as parabens.

Staining of the Tissue with Fuchsine

Tissue staining to detect free aldehyde groups uses an acidic solution of rosaniline hydrochloride (fuchsine). The staining takes advantage of the formation of bonds between the $NH_2$ groups of the dye and the free aldehyde groups on the tissue.

At first, the solution is colorless but in the presence of free aldehyde groups a violet color develops. This is a qualitative evaluation of the availability of free aldehyde groups, after the various treatments.

The samples to stain were cut to obtain cards with dimensions of about 1.5×1.5 cm and successively immersed in the staining solution, about 10 ml, each card in a separate test tube.

The staining solution was 1.00% rosaniline hydrochloride, 4.00% sodium metabisulfite in 0.25 M hydrochloric acid. The samples remained immersed in the stain for 5 minutes at room temperature, with gentle agitation.

Each sample was then transferred to a solution obtained mixing 8 gr of $Na_2SO_3$ and 30 ml of 37% hydrochloric acid, brought to one liter with demineralized water. The samples remained immersed for 10 minutes in this wash solution, with mild agitation.

The samples were then subjected to 2 successive 10 minute washings, with mild agitation in a wash solution including 700 ml of ethanol and 30 ml of 37% hydrochloric acid, brought to one liter with demineralized water.

The washings removed stain that was non-specifically bound to the tissue. About 20 ml of wash solution was used at each change.

When finished the samples were transferred to phosphate buffer pH 7 and photographed to document the different staining.

Reflectance Spectroscopy

The stained samples were subjected to reflectance spectroscopy to quantitatively evaluate the different chromatic characteristics of the fuchsine staining.

Reflectance spectroscopy is a technique for optical investigation based on measurement of the spectral reflectance factor of the surface of a sample as a function of the wavelength of incident radiation. The reflectance parameter is expressed as the ratio of the intensity of the reflected radiation and the incident radiation, as a function of wavelength.

Reflectance measurements were carried out at a wavelength of 570 nm using a Perkin Elmer Lambda 35 spectrophotometer with a spherical integrator.

On a scale of values, a lower reflectance value indicates a more intense sample staining and on the contrary a higher reflectance value indicates a weak staining intensity.

Determination of the Contraction Temperature

The contraction temperature is an index of the level of cross linking of the fixed tissue and was determined on disks of pericardium of about 5 mm diameter, using a scanning differential calorimeter (DSC)Q100 TA Instruments with the following parameters:

nitrogen flow of 50 ml/min,
heating ramp of 5° C./min,
temperature interval between 65° C. and 95° C.

Results

Detoxification

The efficacy of the method described herein, and therefore of the reaction that takes place between the amino groups of the detoxifying molecule and the aldehyde groups on the fixed tissue, is demonstrated by staining the aldehyde groups remaining free with fuchsine; more intense staining indicates numerous free aldehyde groups and, on the contrary, weaker or absent staining indicates few or no free aldehyde groups on the detoxified tissue.

Figure 1B:
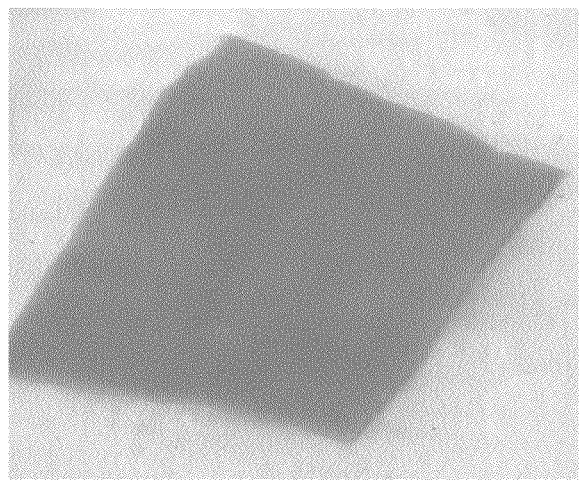
FIG. 1B shows fuchsine staining of a sample that was fixed and detoxified according to the known art using a homocysteic acid solution.
Figure 1C:
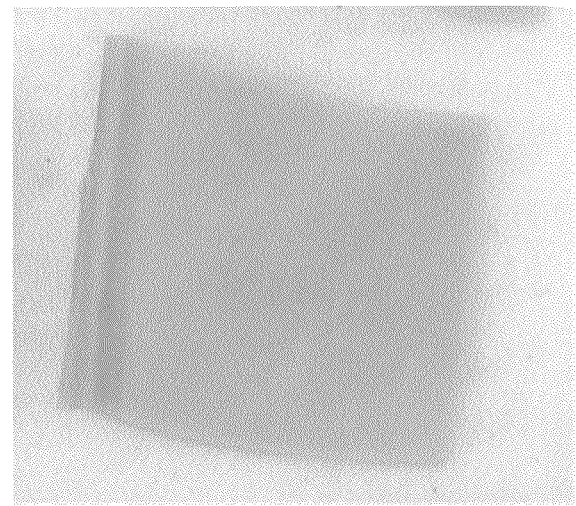
FIG. 1C shows fuchsine staining of a sample that was fixed and detoxified with a taurine solution in accordance with embodiments of the present invention.

FIGS. 1A-1C show a different intensity of staining of a sample detoxified with a solution containing homocysteic acid, sample B, and of a sample detoxified with a solution containing taurine, sample C. A sample not detoxified, sample A, has an intense purple color. The intensity of staining of sample B is less than that of the control sample, but the staining of sample C is very weak if not absent.

The number of free aldehyde groups present on the sample exposed to a solution containing taurine is therefore decidedly lower than that of a sample not detoxified after fixation. Furthermore, treatment with taurine is significantly more efficacious than that carried out with homocysteic acid.

These observations are confirmed by the reflectance spectroscopic analysis of the samples. The reflectance of each sample depends on the staining intensity and by analysis carried out with a spectrophotometer, it is possible to associate a percent reflectance value to each sample.

A higher reflectance value is associated with weaker staining intensity and vice versa a lower reflectance value is related to a greater staining intensity.

As can be seen from the results reported in table 1, the reflectance analyzed at a wavelength of 570 nm and expressed as a percent shows a value of 6.5 for the non detoxified sample shown in FIG. 1A, an intermediate value for the sample detoxified with homocysteic acid shown in FIG. 1B and a decidedly higher value for the sample detoxified with a solution containing taurine shown in FIG. 1C.

TABLE 1

| Sample | Staining observed | Reflectance % at 570 nm |
|---|---|---|
| A-non detoxified | Very intense purple | 6.5 |
| B-homocysteic acid room temperature | Violet | 9.2 |
| C-taurine room temperature | Pale violet | 13 |

These results confirm that treatment with taurine is more efficacious than treatment with homocysteic acid in neutralizing free aldehyde groups on the fixed tissue.

With reference to FIGS. 2A-2D, it can be seen how modifying the temperature conditions under which the sample detoxification is carried out with the solution containing taurine increases the efficacy of the treatment. The staining intensity of the sample detoxified at 40° C., sample C, is weaker with respect to that of the sample detoxified at room temperature, sample B. Even more evident results are obtained by performing the detoxifying treatment at a temperature of 50° C.; in fact, sample D has a staining of decidedly lower intensity indicating that fewer free aldehyde groups remaining, and therefore sites for binding and accumulation of calcium, with respect to the other treatments.

The results of reflectance spectroscopic analysis for the samples shown in FIGS. 2A-2D are presented in table 2. The highest reflectance value, equal to 22, is from a sample having a staining intensity almost absent, that is the sample treated with taurine at 50° C. The non detoxified sample, which has very intense staining, has the lowest reflectance value. The sample treated with taurine at room temperature has a higher value than the non detoxified control, but lower than the sample treated with taurine at 40° C.

TABLE 2

| Sample | Staining observed | Reflectance % at 570 nm |
|---|---|---|
| A-non detoxified | Very intense purple | 6.5 |
| B-taurine room temperature | Pale violet | 12 |
| C-taurine 40° C. | Pink | 17 |
| D-taurine 50° C. | Completely colourless | 22 |

Also in this case the reflectance spectroscopy results confirm that treatment with taurine has a greater detoxifying capacity when conducted at a temperature higher than room temperature.

Contraction Temperature

To verify that the detoxifying treatment does not alter the cross linking of the biological tissue obtained by means of immersion in a solution containing glutaraldehyde, the contraction temperature of tissue detoxified by means of treatment with a solution containing taurine was compared to the contraction temperature of control tissue fixed and not detoxified.

The contraction temperature of tissues immersed in the solution containing taurine at room temperature or at 40° C. are indistinguishable from the contraction temperature of the non detoxified tissue, that temperature being 85-86° C. Therefore, neither treatment has significant effects on the level of tissue cross linking.

The contraction temperature of tissue immersed in the solution containing taurine at 50° C. remains the same as that of the non detoxified tissue (85-86° C.) if the treatment period does not exceed 7-8 hours.

Without prejudice to the underlying principle of the invention, the details and the embodiments may vary, even appreciably, with reference to what has been described by way of example only, without departing from the scope of the invention as defined by the annexed claims.

We claim:

1. A method of treating a biological tissue for use in a biological prosthesis, the method comprising the steps:
    fixation of the biological tissue via a treatment with a solution containing about 0.5% v/v glutaraldehyde in phosphate buffer at room temperature and a pH of 7.4;
    detoxification of the fixed biological tissue via a treatment with a solution containing about 0.70% w/v taurine in phosphate buffer at a temperature between 40° C. and 50° C. and a pH about 7; and
    washing of the detoxified fixed biological tissue in phosphate buffer at room temperature and a pH of 7;
    wherein the detoxification of the fixed biological tissue at a temperature greater than room temperature reduces the number of free aldehyde groups present on the fixed biological tissue when compared to detoxification of fixed biological tissue at room temperature.

2. The method according to claim 1, wherein the detoxification step is carried out at a temperature of 40° C.

3. The method according to claim 1, wherein the detoxification step is carried out for a period in the range of 2 to 96 hours.

4. The method according to claim 1, wherein the detoxification step is carried out for a period of 12 to 48 hours.

5. The method according to claim 1, wherein the detoxification step is carried out for a period of 24 hours.

6. The method according to claim 1, further comprising washing of the fixed biological tissue prior to detoxification, the washing occurring at room temperature.

7. The method according to claim 1, wherein the detoxification step is carried out at a temperature of 50° C.

8. The method according to claim 7, wherein the detoxification step is carried out at a temperature of 50° C. for a period that does not exceed 7 to 8 hours.

9. The method according to claim 1, wherein the detoxification of the fixed biological tissue at a temperature greater than room temperature does not affect a contraction temperature of the fixed biological tissue when compared to a contraction temperature of non-detoxified tissue.

10. A method of treating a biological tissue for use in a biological prosthesis, the method comprising the steps:
    fixation of the biological tissue via a treatment with a solution including about 0.5% v/v glutaraldehyde in phosphate buffer at a pH of 7.4;
    detoxification of the fixed biological tissue via a treatment with a solution including
    about 0.70% w/v taurine in phosphate buffer at a temperature between 20° C. and 50° C. and a pH about 7; and
    washing of the detoxified fixed biological tissue at room temperature and in phosphate buffer at a pH of 7;
    wherein the detoxification of the fixed biological tissue using a solution including taurine binds a greater number of free aldehyde groups present on the fixed biological tissue when compared to detoxification of fixed biological tissue using a solution that consists of homocysteic acid.

11. The method according to claim 10, wherein the detoxification step is carried out at a temperature of 20° C.

12. The method according to claim 10, wherein the detoxification step is carried out at a temperature of 40° C.

13. The method according to claim 10, wherein the detoxification step is carried out at a temperature of 50° C.

14. The method according to claim 10, wherein the detoxification of the fixed biological tissue using a solution including taurine does not affect the contraction temperature of the fixed biological tissue when compared to a contraction temperature of non-detoxified tissue.

* * * * *